(12) United States Patent
Adachi et al.

(10) Patent No.: US 6,643,544 B1
(45) Date of Patent: Nov. 4, 2003

(54) IONTOPHORESIS DEVICE (75) Inventors: Hirotoshi Adachi, Tsukuba (JP); Kazuya Katagai, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/958,602

(22) PCT Filed: Apr. 6, 2000

(86) PCT No.: PCT/JP00/02234
§ 371 (c)(1), (2), (4) Date: Oct. 12, 2001

(87) PCT Pub. No.: WO00/61218
PCT Pub. Date: Oct. 19, 2000

(30) Foreign Application Priority Data

Apr. 12, 1999 (JP) .............................. 11-104576

(51) Int. Cl.[7] ................................. A61N 1/30
(52) U.S. Cl. ....................................... 604/20
(58) Field of Search ............ 604/20, 501; 607/149–153

(56) References Cited

U.S. PATENT DOCUMENTS

| 5,158,537 | A | * | 10/1992 | Haak et al. | .................... 604/20 |
|---|---|---|---|---|---|
| 5,582,587 | A | * | 12/1996 | Gyory et al. | .................... 604/20 |
| 5,817,044 | A | * | 10/1998 | Evers et al. | .................... 604/20 |
| 5,908,400 | A | * | 6/1999 | Higo et al. | .................... 604/20 |
| 5,947,920 | A | * | 9/1999 | Beck | ............................ 604/20 |
| 6,104,950 | A | * | 8/2000 | Higo et al. | .................... 604/20 |
| 6,223,075 | B1 | * | 4/2001 | Beck et al. | .................... 604/20 |
| 6,317,629 | B1 | * | 11/2001 | Haak et al. | .................... 604/20 |
| 6,324,424 | B1 | * | 11/2001 | Ledger et al. | ................ 604/20 |
| 6,374,136 | B1 | * | 4/2002 | Murdock | ...................... 604/20 |

\* cited by examiner

Primary Examiner—Sharon Kennedy
(74) Attorney, Agent, or Firm—Townsend & Banta (57) ABSTRACT

The present invention provides an iontophoresis device and an energization method whereby a prostaglandin can be effectively and continuously administered via a skin or mucosa. The iontophoresis device comprises the first electrode structure (31); the second electrode structure (32); and a power supply (33) electrically connected between the first and the second electrode structures (31), (32). At least one of the first and the second electrode structures contains a prostaglandin and also stabilizing means for inhibiting hydrolysis of the prostaglandin during storage. The power supply (33) is equipped with constant current supplying means and, when both electrode structures contain a prostaglandin, also polarity inverting means. Output current from the power supply may allow the prostaglandin to be delivered to a skin or mucosa.

8 Claims, 2 Drawing Sheets

IONTOPHORESIS DEVICE

TECHNICAL FIELD

The present invention relates to an iontophoresis device and energization method for transdermally or transmucosally delivering prostaglandins to blood vessels surrounding an affected part using electric driving force. In particular, the present invention relates to an iontophoresis device and an energization method, which exhibit good preservation stability for applying prostaglandin E1, or I2 or its derivatives to a patient with chronic artery obstruction (Berger's disease, obstructive arteriosclerosis), vibration disease, progressive systemic sclerosis or systemic lupus erythematodes and which allow for efficient control of delivery for a long period.

BACKGROUND ART

Iontophoresis is a transdermal-absorption promotion system using electricity as external stimulation. It is based on a mechanism that across an electric field generated between an anode and a cathode by energization, molecules with a positive charge move from the anode to the cathode while those with a negative charge move from the cathode to the anode, to generate force, which promotes penetration through a skin barrier by a drug molecule (See, Journal of Controlled Release, Vol. 18, 1992, pp. 213–220; Advanced Drug Delivery Review, Vol. 9, 1992, p.119; Pharmaceutical Research Vol. 3, 1986, pp. 318–326.).

On the other hands, prostaglandins are autacoids biosynthesized in a variety of biological cells, which have been clinically applied to various diseases such as geriatric diseases, thrombotic diseases, inflammatory immunoallergies and digestive ulcers. Since prostaglandins E1 and I2, among them, exhibit pharmacological actions such as potent vasodilator action and platelet-agglutination inhibiting action, they have been used treatment for ameliorating extremity ulcers in chronic arterial embolism such as Berger's disease and obstructive arteriosclerosis; ameliorating resting pain; ameliorating subjective symptoms associated with peripheral hematogenous disorder in vibration disease; recovering peripheral circulation function, neurological function or motor function in a variety of disorders; and ameliorating cutaneous ulcers in progressive systemic sclerosis and systemic lupus erythematodes.

Natural prostaglandins E1 and I2 have been developed as an injection due to their chemical stability and inactivation in a lung. Recently, a chemically and biologically stable injection has been developed by encapsulating prostaglandin E1 in lipid microspheres. On the other hand, recent investigation results have demonstrated that prostaglandins E1 and I2 may be chemically modified to be improved in their chemical and biological stability. It has lead to discovery of derivatives with more potent biological activities, resulting in development of drugs which may be orally administered.

However, as these prostaglandins have been investigated, it has been demonstrated that they are biologically controlled because they can exhibit various biological activities and provide potent pharmacological effects in a small amount. It has been, therefore, required to provide a system which can allow for strict drug-delivery control for achieving optimal drug efficacy of these prostaglandins in a limited disease while minimizing their side effects. For example, rimaprost, an oral prostaglandin E1 derivative, exhibits vasodilation, vascular-flow increasing, platelet-agglutination inhibiting and erythrocyte-deformability improving effects, so that it may be effective in ameliorating various ischemic symptoms such as ulcer, pain, frigidity and numbness associated with obstructive thromboanguitis, while excessive administration may causes side effects such as facial flush, tachycardia, extremity cyanosis and hemorrhage. These prostaglandins are, however, generally degraded by digestive fluid in a gastrointestinal tract, hydrolyzed by splitting enzymes in a gastrointestinal tract wall and inactivated mainly in a lung by first-pass effect. Furthermore, these prostaglandins have a short in vivo half life, so that drug efficacy cannot be adequately controlled in oral administration. Specifically, in oral administration, compliance may be improved in comparison with injection while a blood level control may be more difficult than injection administered by infusion. It is eminent particularly when the above prostaglandins, specifically prostaglandins E1 and I2 or their derivatives are continuously administered to enhance therapeutic effect. When a patient with a local lesion (in particular, an extremity lesion) such as cutaneous ulcer is treated via blood, for example, by an injection or oral drug, a drug may not be sufficiently delivered to the lesion to achieve satisfactory therapeutic effect.

As pharmaceutically practical dosage forms for these prostaglandins, there have been investigated, besides injections, oral formulations and suppositories for achieving systemic effect, transdermal and transmucous administration using ointments, creams, lotions and patches for achieving local effect. For example, Japanese Patent Application Laid-Open No.7-277985 has disclosed a transdermal absorption formulation to be applied to a cutaneous ulcer lesion. Since prostaglandins exhibit lower transdermal absorbability, a variety of transdermal-absorption promotion methods have been studied for improving absorbability. For example, Japanese Patent Application Laid-Open No. 3-83925 has disclosed the use of a transdermal-absorption promoter. In these existing formulations, local administration systems have been, however, dominant, aiming at direct administration on an ulcer lesion in a cutaneous surface. Furthermore, there have been no studies for a formulation by which long-term absorption may be achieved.

On the other hands, iontophoresis has been intensely investigated, which is a novel drug delivery system in place of an injection as an administration system for a drug requiring strict administration control. If an iontophoresis formulation by which absorption to the same level as that in an injection may be achieved and which allows a patient to administer a drug by him/herself is developed, home treatment may be realized. Precise control of an energization time in iontophoresis may allow any drug-absorption pattern to be achieved. In particular, it may lead to more effective drug treatment in a drug requiring administration control.

In terms of prostaglandin administration using such iontophoresis, Japanese Patent Application Laid-Open No. 9-235230, for example, has disclosed that combining prostaglandin E1 with a cyclodextrin may be improve drug stability and a transdermal absorption rate. International Patent Publications WO 98/29157 and WO 98/29158 have disclosed local administration of a prostaglandin for treating impotence by iontophoresis.

Conventional techniques such as ointments and creams are, however, related to a local-administration formulation mainly for treating diseases in a cutaneous surface without expecting sustained effects so that these techniques are not effective to diseases without ulcer. Iontophoresis for prostaglandins disclosed in Japanese Patent Application Laid-Open No. 9-235230 and International Patent Publications WO 98/29157 and WO 98/29158 is not for long-term delivery, may not allow us to strictly control absorption and thus is not sufficient to realize effective drug delivery.

DISCLOSURE OF THE INVENTION

It is an object of the present invention to provide an iontophoresis device and an energization method whereby prostaglandins can be effectively and continuously delivered via a skin or mucosa.

The inventors have intensely conducted investigation for achieving the above objective and have finally found that stabilizing means is incorporated in an iontophoresis device to improve preservation stability of prostaglandins, that constant-current supplying means is used to effectively and continuously administer via a skin or mucosa even a small amount of prostaglandin, and that constant-current supplying means may be combined with polarity inverting means to maintain electrificability for a long period so that a drug can be administered with good reproducibility and an improved bioavailability.

An iontophoresis device according to the present invention transdermally or transmucosally administers a prostaglandin and comprises:

(a) a first electrode structure containing a prostaglandin;

(b) a second electrode structure; and (c) a power supply electrically connected between the first and the second electrode structures and equipped with constant-current supplying means, wherein the first electrode structure comprises stabilizing means for inhibiting hydrolysis of the prostaglandin during storage.

The second electrode structure may contain a prostaglandin. In such a case, the power supply is, in addition to the constant-current supplying means, equipped with polarity inverting means.

The above stabilizing means may be, for example, a drug retainer which retains a prostaglandin in a dry condition. The stabilizing means may comprise a stabilizing agent for chemically stabilizing a prostaglandin or a dissolution promoter. Examples of prostaglandins include prostaglandins E1 and I2 as well as their derivatives. These prostaglandins may comprise at least one of a surfactant for promoting drug delivery and a water-soluble cyclodextrin.

An energization method for iontophoresis may be conducted by attaching the first and the second electrode structures to an extremity. When one of the first and the second electrode structures contains a prostaglandin, the power supply continuously applies pulse direct current or pulse depolarization direct current for a total period of 1 hour to 24 hours. When both of the first and the second electrode structures contains a prostaglandin, the power supply continuously applies direct current, pulse direct current or pulse depolarization direct current for a total period of 1 hour to 48 hours with a polarity inversion period of less than 4 hours. Such continuous energization is preferably conducted in the range of 3 to 7 days per week.

Such a configuration may provide an iontophoresis device and an energization method whereby prostaglandins can be effectively and continuously delivered via a skin or mucosa.

BEST MODE FOR CARRYING OUT THE INVENTION

The present invention will be described in detail with reference to the drawings when necessary.

An iontophoresis device according to the present invention stably comprises stabilizing means, whereby a prostaglandin is chemically stabilized for improving storage and electric stability. A surfactant or water-soluble cyclodextrin is added to a device to promote drug delivery and a constant current is used, so that even a small amount of drug may be effectively and continuously absorbed. Constant-current supplying means and polarity inverting means are combined to maintain electrificability for a long period so that a drug may be transdermally administered with a higher bioavailability and good reproducibility in local treatment of cutaneous ulcer. There are no restrictions to a way for reinforcing a patch constituting such a device, i.e., a backing composition, its structure, etc.

Any prostaglandin may be used in the present invention, which has pharmacological effect such as vasodilation effect and platelet-agglutination inhibiting effect and may be used in treatment for ameliorating extremity ulcers in chronic arterial embolism such as Berger's disease and obstructive arteriosclerosis; ameliorating resting pain; ameliorating subjective symptoms associated with peripheral hematogenous disorder in vibration disease; recovering peripheral circulation function, neurological function or motor function in a variety of disorders; and ameliorating cutaneous ulcers in progressive systemic sclerosis and systemic lupus erythematodes. As an prostaglandin, there are prostaglandin E1 (alprostadil), rimaprost, clopidogrel sulfate, beraplost, cyprostene, iroprost, ataprost, clinprost and ethyl icosapentate; more preferably, chemically stabilized prostaglandin E1 and prostaglandin I2 or their derivatives; that is, alprostadil alphadex, rimaprost, clopidogrel sulfate, beraplost, cyprostene, iroprost, ataprost and clinprost, may be used.

An electrode structure used in the present invention, which is not limited to any particular structure, comprises means for retaining an active ingredient which in turn comprises stabilizing means for inhibiting hydrolysis of the active ingredient during storage. As the electrode structure, a matrix type electrode structure where an active ingredient is dispersed in a conductive gel and a stacked electrode structure whereby a higher level of an active ingredient can be applied to a skin surface contacting to the structure, may be exemplified.

For example, a matrix type electrode structure may comprise an electrode consisting of an active electrode and an active-ingredient retaining means in which a prostaglandin and a stabilizing agent for chemically stabilizing the prostaglandin are dispersed in a hydrophilic conductive gel. A stacked electrode structure may comprise, for example, an electrode layer consisting of an active electrode, a hydrophilic gel layer and an active-ingredient retaining means containing a prostaglandin which is separated from the hydrophilic conductive gel layer. In the stacked electrode structure, the system may be activated by making the retaining means containing prostaglandin, which is separated in dry condition, in contact with the hydrophilic gel layer when used. In particular, a stacked electrode structure in which a retaining means containing a prostaglandin before use can be stored while being dried and separated is a device which can be applied to a variety of prostaglandins because it can maintain stability during storage for a long period. Furthermore, in a stacked electrode structure, a stabilizing agent or dissolution promoter may be added to a separation retaining means which can separate and store an active ingredient to allow the ingredient to be stored for a much longer period. In particular, a stacked electrode structure exhibiting good stability of an active ingredient is more preferable in the present invention.

Stabilizing means in an electrode structure is used for improving stability of a prostaglandin during storage and during iontophoresis energization. As the stabilizing means, chemical modification of a prostaglandin such as natural prostaglandins E1 and I2 and incorporating a stabilizing system in an electrode structure to achieve stabilization, may be exemplified. As used herein, a stabilizing system incorporated in an electrode structure refers to, for example, a drug retainer which can separate and store a prostaglandin in a dried state for inhibiting its hydrolysis. Furthermore, a stabilizing agent or dissolution promoter may be added to the drug retainer to improve drug stability and drug absorbability. In a structure equipped with a drug retainer, a drug in the drug retainer is dissolved when used so that its solubility and dissolving rate must be improved. There are no restrictions to a stabilizing agent for inhibiting hydrolysis of a prostaglandin and a dissolution promoter. As the agent, saccharides such as glucose, maltose, fructose, galactose, mannitol, sorbitol, mannose, glucosamine, lactose, sucrose, trehalose, natural cyclodextrins (e.g., α-cyclodextrin, β-cyclodextrin and γ-cyclodextrin) and water-soluble cyclodextrin derivatives having a substituent including hydroxypropyl, glycolyl, maltosyl, sulfate, phosphate, carboxyl, carboxymethyl, carboxymethylethyl and/or amino; organic acids such as citric acid, lactic acid, tartaric acid, succinic acid and their salts; surfactants such as polyoxyethylene hydrogenated castor oil 60, polyoxyethylenesorbitan monooleate, polyoxyethylenesbrbitan monolaurate, polyoxyethylenelauryl ether, polyoxyethyleneoctyl phenyl ether, polyoxyethylenenonyl phenyl ether, polyoxyethylene polyoxypropylene glycol, polysorbate and saccharose aliphatic acid ester; pH regulators; water absorptive polymers; desiccants such as silica gel and zeolite, may be exemplified. These may be combined for higher effect.

There are no restrictions to a conductive material constituting an electrode, but an active electrode exhibiting good stability of an active ingredient during energization is preferable. An active electrode refers to an electrode where during energization to a composition generally used in iontophoresis a redox reaction occurs with a voltage lower than that required for electrolysis of water without generation of, e.g., oxygen gas in an anode or hydrogen gas in a cathode or associated pH variation. It maybe silver, aluminum, zinc, copper or iron for an anode while silver, silver chloride or a mixture containing them for a cathode. Particularly, silver or silver-silver chloride exhibits good electric properties such as a resistance and may be produced with a lower cost and a higher productivity when being produced using a paste material. Furthermore, for reducing the amount of an active electrode material and a production cost, the active electrode paste material may be blended with an inexpensive carbon paste or the active electrode paste material may be applied only to a required area on a carbon surface. In these electrodes, a solution pH does not vary so that it is quite safe in terms of skin irritation.

Further, as a hydrophilic conductive gel constituting an electrode, gel or solution type is not limited, but it is desirable to use a gel in the light of productivity. As a hydrophilic conductive gel, synthetic polymers such as polyacrylic acid, poly(sodium acrylate), methoxyethylene-maleic anhydride copolymer, methoxyethylene-maleic acid copolymer, isobutylene-maleic anhydride copolymer, isobutylene-maleic acid copolymer, N-vinylacetamide-sodium acrylate copolymer, carboxyvinyl polymer, polyvinyl alcohol, polyvinylpyrrolidone and polyacrylamide; polysaccharides such as agar, starches, mannan, xanthan gum, locust bean gum, carageenan, gellant gum, tamarind gum, curdlan, pectin, falseleran, guar gum, alginic acid, sodium alginate, tarra gum, karaya gum, gum arabic, cellulose and their derivatives; and gellatins, may be exemplified, which may be used alone or in combination of two or more.

To a hydrophilic conductive gel used, an electrolyte may be added for imparting conductivity, pH regulation, buffering and skin-protection effect. As the electrolyte, citric acid, sodium citrate, calcium citrate, acetic acid, sodium acetate, potassium acetate, phosphoric acid, disodium hydrogen phosphate, sodium dihydrogen phosphate, polyphosphoric acid, potassium chloride, sodium chloride, calcium chloride, glucosamine hydrochloride, monoethanolamine, diethanolamine, triethanolamine, tromethamol, meglumine, lactic acid, sodium lactate, triethanolamine hydrochloride, hydrochloric acid, sodium hydroxide, calcium hydroxide, potassium hydroxide, a cation exchange resin having an acetate or sulfonate group as a functional group and an anion exchange resin having quaternary ammonium group as a functional group and their salts, primary to tertiary amines or polymers/resins including them, cholestyramine, acidic amino acids such as aspartic acid and glutamic acid, basic amino acids such as arginine, lysine and histidine, other amino acids such as arginine hydrochloride, L-glutamine, sodium L-glutaminate, and polyamines, may be used. Further, stabilizers, thickeners, wetting agents, surfactants, solubilizing agents, solubilizing aids, moisturizing agents and absorption promoters may be added depending on the necessity.

Retaining means for an active ingredient in a matrix type electrode structure used in the present invention retains a drug by dispersing (e.g., dissolution or suspension) it in a member comprising the above hydrophilic conductive gel or having a porous or capillary structure of various types (hereinafter, sometimes simply referred to as a "porous material") through which the drug can penetrate. The hydrophilic conductive gel and the porous material may be combined. In addition, when the structure comprises a chemically unstable active ingredient, the retaining means may be kept dried and then activated by a variety of dissolving liquid when used. As the porous material, organic porous materials including natural fibers such as cellulose; semi-synthetic fibers such as cellulose acetate, nitrocellulose and rayon; a fiber assembly formed by polyethylene, polypropylene, polyethylene terephthalate, nylon, polyester or a synthetic fiber prepared by chemical modification of these materials; a sheet such as a paper; a cloth such as fabrics and nonwoven fabrics; and porous synthetic resins such as porous polypropylene, porous polystyrene, porous poly(methyl methacrylate, porous polyesters, porous nylon, porous polysulfones, porous fluororesins, porous polyvinyl alcohols and porous polyurethanes, may be used. There are no restrictions to a type or combination for materials as long as the above hydrophilic gel or dissolving liquid may be impregnated.

Figure 1:
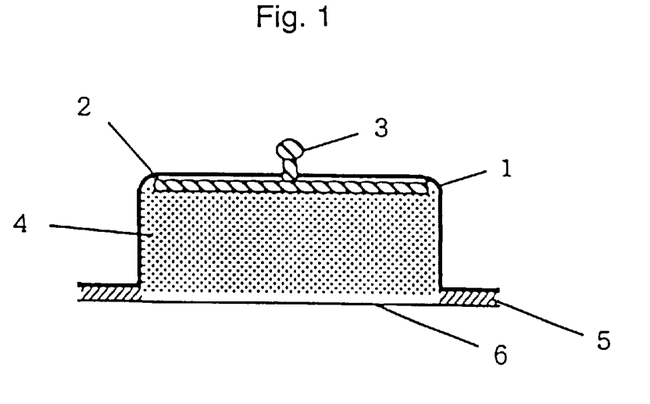
FIG. 1 is a cross section illustrating an embodiment of a matrix type electrode structure according to the present invention.

A matrix type electrode structure used in the present invention is one of those which are most universal for transdermally administrating a drug by iontophoresis using a variety of applicators applicable to a skin and is useful. FIG. 1 is a cross section illustrating an embodiment of a matrix type electrode structure having the above configuration.

In FIG. 1, the basic part of the applicator is comprised of a backing 1 having a cylindrical pit (made of polypropylene, inner diameter: 30 mm), a circularly punched printed silver electrode 2 fitting the bottom of the pit (diameter: 25 mm; thickness: 0.04 mm), an adhesive sheet 5 having a hole with a diameter of 30 mm (NITTO TAPE, manufactured by Nitto Denko Co.), a hydrophilic conductive gel layer 4 in which a drug is dispersed (Agar UP-16, manufactured by Ina Foods Co.) and a liner 6 for preventing water from evaporating during storage. A connection terminal 3 is attached to the electrode 2 through a small hole opening in the center of the backing 1 such that the electrode is connected to a power supply. When used, the liner 6 is removed to make the hydrophilic conductive gel layer 4 in contact with a skin.

An area of the above matrix type electrode structure may be appropriately selected, depending on a retained amount of a drug, an administration site and a treated area; for example about 0.5 to 100 cm$^2$, preferably about 1 to 50 cm$^2$. The retained amount of a drug may be an effective amount depending on the type of the drug, the type of a drug retainer and an administration site; for example, about 0.001 to 500 mg, preferably about 0.01 to 100 mg per one gram of the drug retainer.

The retaining means of an active ingredient in a stacked electrode structure may be a member having a porous or capillary structure (hereinafter, sometimes referred to as a "porous material") which may be selected from a variety of types and can retain the drug and through which the drug can penetrate, or a combination of such members. As the porous material, organic porous materials including natural fibers such as cellulose; semi-synthetic fibers such as cellulose acetate and nitrocellulose; a fiber assembly formed by polyethylene, polypropylene, nylon, polyester or a synthetic fiber prepared by chemical modification of these materials; a sheet such as a paper; a cloth such as fabrics and nonwoven fabrics; and porous synthetic resins such as porous polypropylene, porous polystyrene, porous poly(methyl methacrylate), porous nylon, porous polysulfones and porous fluororesins, may be used. Such a porous material may be hard, but is often flexible or plastic. A stack device may exhibit higher bioavailability in a drug having potent pharmacological effect in a small amount like a prostaglandin and it may, therefore, allow us to more effectively utilize the drug.

Figure 2:
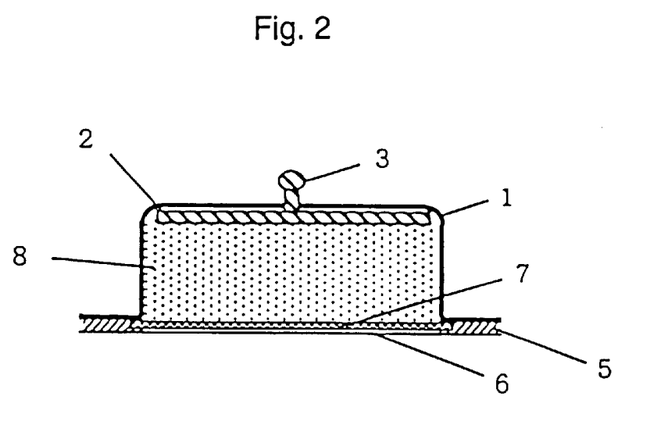
FIG. 2 is a cross section illustrating an embodiment of a stacked electrode structure according to the present invention.

There are no restrictions to a shape of the active-ingredient retaining means as a drug layer, but it may be a sheet. A thickness of the sheet may be appropriately selected, depending on some factors such as the amount of the drug to be retained. It may be, for example, about 1 to about 500 μm, preferably about 10 to about 200 μm. An area of the drug layer may be appropriately selected, depending on some factors such as the amount of the drug to be retained, an administration site and a treatment area; for example, about 0.5 to 100 cm$^2$, preferably about 1 to 50 cm$^{2.}$ A stacked electrode structure used in the present invention is one of those which are most universal for transdermally administrating a drug by iontophoresis using a variety of applicators applicable to a skin and is useful. FIG. 2 is a cross section illustrating an embodiment of a stacked electrode structure having the above configuration.

In FIG. 2, the basic part of the applicator is comprised of a backing 1 having a cylindrical pit (made of polypropylene, inner diameter: 30 mm), a circularly punched printed silver electrode 2 fitting the bottom of the pit (diameter: 25 mm; thickness: 0.04 mm), ahydrophilic conductive gel layer 8 (Agar UP-16, manufactured by Ina Foods Co.), an adhesive sheet 5 having a hole with a diameter of 30 mm (NITTO TAPE, manufactured by Nitto Denko Co.), a drug layer 7 attached to the sheet 5 (diameter: 35mm, thickness: 0.125 mm; CMF film; manufactured by Advantech Inc.) and a liner 6 for preventing water from evaporating during storage. A connection terminal 3 is attached to the electrode 2 through a small hole opening in the center of the backing 1 such that the electrode is connected to a power supply. When used, the liner 6 is removed to make the drug layer 7 in contact with a skin. Alternatively, the drug layer 7 is separated from the adhesive sheet 5 before use and when used, it is attached to the sheet.

A retained amount of a drug may be an effective amount depending on the type of the drug, the type of the drug layer such as a conductive gel and a porous material and an administration site; for example, about 0.001 to 200 mg, preferably about 0.01 to 10 mg per 1 cm$^2$of the drug retainer.

As a materials for promoting drug delivery in the present invention, a water-soluble material such as surfactants and water-soluble cyclodextrins, may be exemplified. Such a water-soluble material is added to a hydrophilic conductive gel or separation retaining means. Furthermore, the material is effective in improving solubility of a drug. As the water-soluble material, surfactants such as polyoxyethylene hydrogenated castor oil 60, polyoxyethylenesorbitan monooleate, polyoxyethylenesorbitan monolaurate, polyoxyethylenelauryl ether, polyoxyethyleneoctyl phenyl ether, polyoxyethylenenonyl phenyl ether, polyoxyethylene polyoxypropylene glycol, polysorbate and saccharose aliphatic acid ester; saccharides such as glucose, maltose, fructose, galactose, mannitol, sorbitol, mannose, glucosamine, lactose, sucrose and trehalose; water-soluble cyclodextrins including natural cyclodextrins such as α-cyclodextrin, β-cyclodextrin and γ-cyclodextrin, water-soluble cyclodextrin derivatives having a substituent including hydroxypropyl, glycolyl, maltosyl, sulfate, phosphate, carboxyl, carboxymethyl, carboxymethylethyl and/or amino, and cyclodextrin polymers; water-soluble polymers such as starches, dextran, dextran sulfate, inulin and polyvinylpyrrolidone; and wetting agents such as glycerol, ethyleneglycol, polyethyleneglycol, propyleneglycol, butyleneglycol, urea, ethylurea, urea derivatives, methylpyrrolidone and pyrrolidone derivatives, may be exemplified. Among them, water-soluble materials such as surfactants and water-soluble cyclodextrins are preferable.

Figure 3:
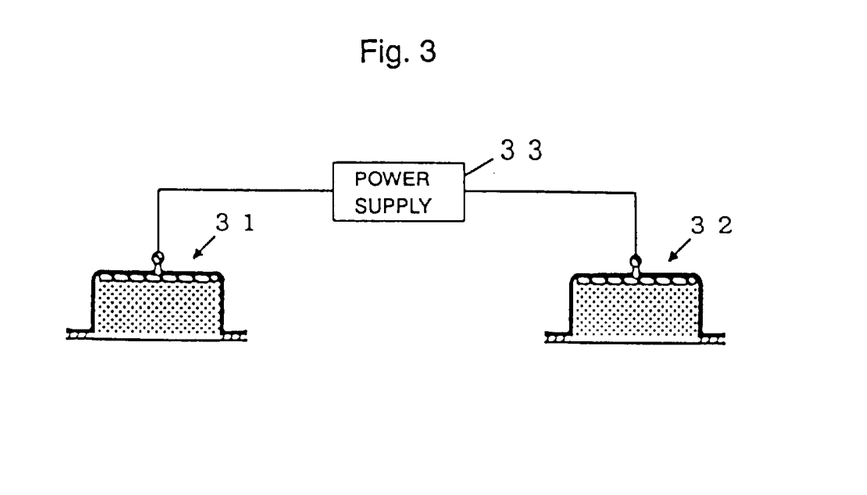
FIG. 3 schematically shows an embodiment of an iontophoresis device according to the present invention.

As shown in FIG. 3, a transdermal or transmucous drug delivery system based on an iontophoresis device according to the present invention comprises the above electrode structure (the first electrode structure) 31, a counter electrode structure (the second electrode structure) 32 and a power supply 33 equipped with constant-current supplying means. As used herein, a current from the power supply 33 means transmitted current involved in drug absorption and may be direct current, pulse direct current or pulse depolarized direct current. The power supply may be selected from those which can apply continuous dc voltage or pulse dc voltage, preferably those which can apply pulse dc voltage, particularly those which can apply rectangular pulse dc voltage. A frequency of pulse dc voltage may be appropriately selected from the range of preferably 0.1 to 200 kHz, more preferably 1 to 100 kHz, particularly 5 to 80 kHz. A ratio between ON/OFF in pulse dc voltage may be appropriately selected from the range of 1/100 to 20/1, preferably 1/50 to 15/1, more preferably 1/30 to 10/1. An energization period may be 48 hours or less, preferably 1 to 24 hours for continuous energization and 48 hours or less, preferably 1 to 24 hours in total for intermittent energization.

In the device, the second electrode structure 32 may also comprise a drug to have the same device configuration as the second electrode structure 32 and the first electrode structure 31. Herein, an active electrode may be made of silver, silver chloride or a mixture containing them and a power supply 33 having constant current supplying means may be equipped with polarity inverting means to allow absorption to be controlled for a long period. Positive/negative polarity may be inverted using the polarity inverting means to save the amount of silver or silver chloride required in response to a polarity inverting period (an interval for inverting energization polarity). More advantageously, a paste may be used as an electrode material to further save a cost. There are no restrictions to a positive/negative polarity inverting period as long as it is within a range where drug absorbability is adversely affected; generally 1 min to 24 hours, preferably 1 min to 6hours, more preferably 1 min to 2hours. A total energization period is generally 1 to 72 hours, preferably 1 to 48 hours, more preferably 1 to 24hours. For intermittent energization, an energization period is 1 to 72 hours, preferably 1 to 48 hours, more preferably 1 to 24 hours in total. During energization, a polarity inversion period is generally constant, but it may be varied as appropriate. Using the polarity inverting means may allow us to conduct energization for a long period. Furthermore, both of the first electrode structure 31 and the second electrode structure 32 comprise an active ingredient so that a treatment area may be increased, resulting in higher therapeutic effect in a drug exhibiting local blood-flow improvement effect like a prostaglandin.

In treatment using iontophoresis with the above prostaglandins, a drug is preferably administered as a sustained dosage form; preferably with a regimen of 3 to 7 days per week. In a disease to be treated, ulcer may be often observed in a local site, particularly an extremity. The above device may be used around the lesion to provide higher therapeutic effect. The above device and energization may be indicated for ameliorating extremity ulcers in chronic arterial embolism such as Berger's disease and obstructive arteriosclerosis; ameliorating resting pain; ameliorating subjective symptoms associated with peripheral hematogenous disorder in vibration disease; recovering peripheral circulation function, neurological function or motor function in a variety of disorders; and ameliorating cutaneous ulcers in progressive systemic sclerosis and systemic lupus erythematodes.

EXPERIMENTAL EXAMPLES

The present invention will be specifically described with reference to, but not limited to, Comparative Examples and Examples according to the following Experimental Examples. In Experimental Example 1, stability of prostaglandin E1 in a matrix type or stacked device was investigated. In Experimental Example 2, control of an iontophoresis constant current for prostaglandin E1 was investigated in an in vitro transdermal penetration test. In Experimental Example 3, effect of an energization period on iontophoresis of prostaglandin E1 was investigated on the basis of drug absorbability and therapeutic effect to a peripheral artery obstruction model. In Experimental Example 4, effect of a polarity inversion period on polarity-inverting iontophoresis was evaluated on the basis of drug absorbability. In Experimental Example 5, an optimal administration method in iontophoresis of prostaglandin E1 was investigated for therapeutic effect to peripheral artery obstruction model.

Experimental Example 1

First, there were prepared a gel for a matrix type device made of a carboxyvinyl polymer, which had been prepared by adding 10 N sodium hydroxide to a 1 w/w% carboxyvinyl polymer to adjust pH to about 7, adding 250 $\mu$g of prostaglandin E1, filling an electrode structure in FIG. 1 with the mixture and enveloping the product with aluminum, for Comparative Example 1; a gel for a matrix type device made of a carboxyvinyl polymer and β-cyclodextin, which had been prepared by adding 10 N sodium hydroxide to a 1 w/w% carboxyvinyl polymer, adding 250 $\mu$g of prostaglandin E1, 100 mg of β-cyclodextrin and an appropriate amount of lactic acid per 1 g of the gel, adjusting pH to about 4, filling an electrode structure in FIG. 1 with the mixture and enveloping the product with aluminum, for Example 1; and a stacked device where prostaglandin E1, β-cyclodextrin and citric acid was dry-retained in a membrane containing cellulose acetate, which had been prepared by impregnating 250 $\mu$g of prostaglandin E1, 2.5 mg of β-cyclodextrin and 20 $\mu$g of citric acid in a CMF film (manufactured by Advantech Inc.) cut into about 5 cm$^2$, drying the film and enveloping the product together with 1 g of a desiccant Ozo (manufactured by Ozo Chemical Tech. Inc.) in aluminum, for Example 2to give samples. In this Experimental Examples, a content of prostaglandin E1 was determined by high performance chromatography for investigating stability of prostaglandin E1 in these Examples and Comparative Example.

Table 1 shows the results of comparison of prostaglandin E1 stabilization in these iontophoresis electrode structures after storage at 60° C. for 1 day. In Comparative Example 1 without adding a stabilizing agent, the remaining amount was reduced to about 2% or less after storage. On the other hand, in Example 1 for a matrix type device to which a stabilizing agent was added, storage stability of prostaglandin E1 was improved to about 85%. In a stacked device in Example 2, stability of prostaglandin E1 was significantly improved, resulting in a remaining amount of about 98%.

TABLE 1

| Experimental Example 1 | Device structure | Remaining rate (%) |
|---|---|---|
| Comparative Example 1 | Matrix type device | <2% (lower than a detection limit) |
| Example 1 | Matrix type device | about 85% |
| Example 2 | Stacked device | about 98% |

Experimental Example 2

In an iontophoresis experiment, a horizontal cell was used and a back skin of a hairless mouse was used as a diaphragm. An electrode structure was a stacked device filled with a 3 w/w% agar gel containing 0.2 w/w% sodium chloride (an electrode used was a silver/silver chloride electrode). A membrane containing cellulose acetate (manufactured by Advantech Inc., CMF film) was used as separation-retaining means. Then, 250 $\mu$g of a prostaglandin E1·α-cyclodextrin clathrate compound was dried and fixed. Before use, the gel was in contact with the membrane and used. This experiment was conducted in an air bath adjusted at 32° C. while an amount of the drug moved to the receptor phase was determined by high performance liquid chromatography at regular intervals. In Examples 3, 4 and 5 and Comparative Example 2, the first electrode structure contained a prostaglandin E1·α-cyclodextrin clathrate compound. In the Examples, pulse depolarized direct current was applied by a short-cut switch for 4 hours (frequency: 50 kHz; duty: 50%) while in Comparative Example the system was left without energization for 4 hours. In Examples 6 and 7 and Comparative Example 3, the first and the second electrode structures contained a prostaglandin E1-α-cyclodextrin clathrate compound (each electrode was a silver/silver chloride electrode). In the Examples, pulse depolarized direct current was applied by a short-cut switch (frequency: 50 kHz; duty: 50%) with one-hour polarity inversion while in Comparative Example the system was left without energization for 4 hours. Table 2 shows details of these Examples and Comparative Examples.

TABLE 2

| Experimental Example 2 | Energization | Constant Current value (mA/cm²) | Total energization or adhesion time | Drug-containing electrode | Polarity inversion period |
|---|---|---|---|---|---|
| Example 3 | Energized | 0.01 | 4 hours | 1st electrode structure | None |
| Example 4 | Energized | 0.05 | 4 hours | 1st electrode structure | None |
| Example 5 | Energized | 0.10 | 4 hours | 1st electrode structure | None |
| Example 6 | Energized | 0.05 | 4 hours | 1st and 2nd electrode structures | 1 hour |
| Example 7 | Energized | 0.10 | 4 hours | 1st and 2nd electrode structures | 1 hour |
| Comparative Example 2 | Not energized | 0 | 4 hours | 1st electrode structure | None |
| Comparative Example 3 | Not energized | 0 | 4 hours | 1st and 2nd electrode structures | None |

Figure 4:
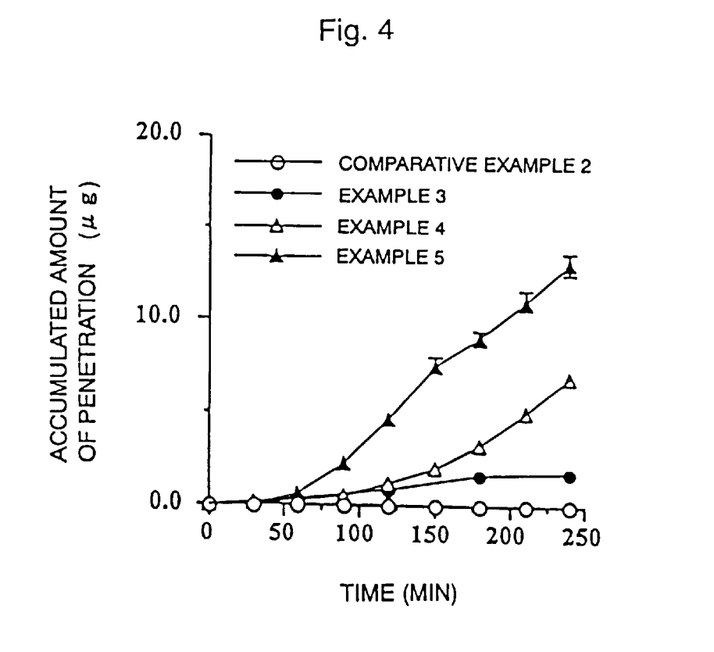
FIG. 4 shows in vitro cutaneous penetration of prostaglandin E1 without polarity inversion in a hairless mouse.
Figure 5:
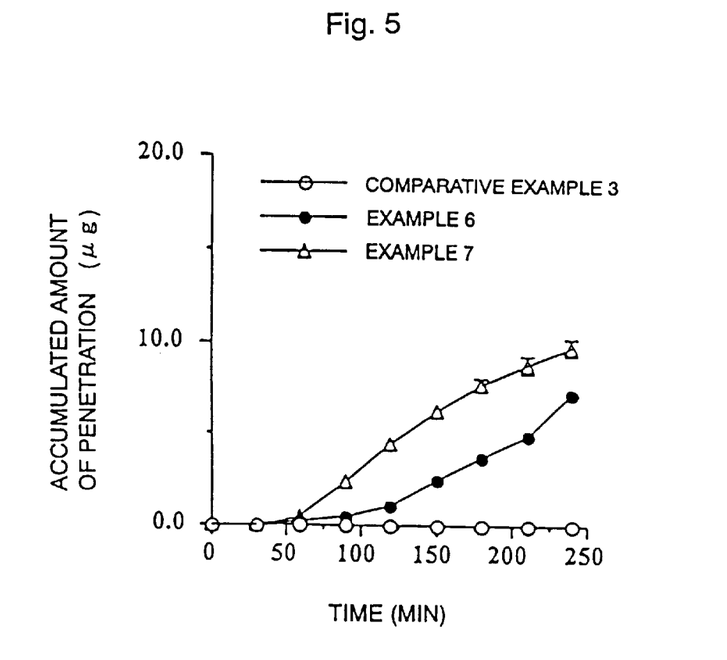
FIG. 5 shows in vitro cutaneous penetration of prostaglandin E1 during polarity inversion in a hairless mouse.

FIGS. 4 and 5 show the results from these Examples and Comparative Examples. As a result, in an iontophoresis group of Examples 3 to 5 (one-way energization) and Examples 6 and 7 (two-way polarity-inverting energization), current-dependent transdermal penetration of prostaglandin E1 was observed, independently of a direction of energization, while in a non-energization group of Comparative Examples 2 and 3, transdermal penetration of prostaglandin E1 was not observed. These results indicate that constant-current control is effective as absorption controlling means for prostaglandin E1 in any energization method.

Experimental Example 3

In Experimental Example 3, effect of an energization period on iontophoresis of prostaglandin E1 was evaluated on the basis of a drug absorption in single dosing and therapeutic effect to a rabbit peripheral artery obstruction model in successive dosing. In evaluation of a drug absorption in single dosing, Japanese white male rabbits (body weight: 2.5 to 3.0 kg) were used and the hair of the animals was removed on their ear skin with an animal clipper. After attaching the electrode structures of Examples and Comparative Examples, the system was electrified according to each Example. At the end of energization, an amount of the remaining drug in the device was determined by high performance liquid chromatography. The drug absorption was calculated by subtracting the remaining amount from the initial content.

In evaluation of therapeutic effect in successive dosing, Japanese white male rabbits (body weight: 2.5 to 3.0 kg) were used and the hair of the animals was removed on their right-ear skin with an animal clipper. Sodium laurate (5 mg, a 5 w/v% ethanol-containing isotonic phosphate buffer) was injected from its posterior auricular artery to induce peripheral artery obstruction. Each prostaglandin-containing formulation was daily applied around an obstruction site. Healing of a lesion was visually observed after 7 days on the basis of the criteria in Table 3.

TABLE 3

| Therapeutic effect in a lesion | |
|---|---|
| +++ | Normal skin condition |
| ++ | Discoloring in a peripheral ear was observed |
| + | Discoloring in a wide area of an ear was observed |
| ± | Lesion in a peripheral ear was observed |
| − | Lesion in a wide area of an ear was observed |

Drug absorption in single dosing was evaluated in Examples 8 to 12 and Comparative Examples 4 and 5, while therapeutic effect in multiple dosing was evaluated in Examples 8 and 10 and Comparative Examples 4 and 5. In Examples 8 and 9 and Comparative Example 4, the first electrode structure contained a prostaglandin E1·α-cyclodextrin clathrate compound (the electrode used was a silver/silver chloride electrode). In Examples 8 and 9, pulse depolarized direct current was applied by a short-cut switch (frequency: 50 kHz; duty: 50%) for 4 or 8 hours while in Comparative Example the system was left without energization for 8 hours. In Examples 10, 11 and 12 and Comparative Example 5, the first and the second electrode structures contained a prostaglandin E1·α-cyclodextrin clathrate compound (each electrode used was a silver/silver chloride electrode). In the Examples, pulse depolarized direct current was applied by a short-cut switch (frequency: 50 kHz; duty: 50%) for 4, 8 and 12 hours, respectively, with polarity inversion period of one hour while in Comparative Example the system was left without energization for 8 hours. In the first and the second electrode structures, a stacked device filled with a 3 w/w% agar gel containing 0.2 w/w% sodium chloride (an electrode used was a silver/silver chloride electrode). A membrane containing cellulose acetate (manufactured by Advantech Inc., CMF film) was used as separation-retaining means. Then, 250 μg of a prostaglandin E1·α-cyclodextrin clathrate compound was dried and fixed. Before use, the gel was in contact with the membrane. Table 4 shows details of these Examples and Comparative Examples.

TABLE 4

| Experimental Example 3 | Energization | Constant Current value (mA/cm²) | Total energization or adhesion time | Drug-containing device | Polarity inversion period |
|---|---|---|---|---|---|
| Example 8 | Energized | 0.10 | 4 hours | 1st electrode structure | None |
| Example 9 | Energized | 0.10 | 8 hours | 1st electrode structure | None |

TABLE 4-continued

| Experimental Example 3 | Energization | Constant Current value (mA/cm²) | Total energization or adhesion time | Drug-containing device | Polarity inversion period |
|---|---|---|---|---|---|
| Example 10 | Energized | 0.10 | 4 hours | 1st and 2nd electrode structures | 1 hour |
| Example 11 | Energized | 0.10 | 8 hours | 1st and 2nd electrode structures | 1 hour |
| Example 12 | Energized | 0.10 | 12 hours | 1st and 2nd electrode structures | 1 hour |
| Comparative Example 4 | Not energized | 0 | 8 hours | 1st electrode structure | None |
| Comparative Example 5 | Not energized | 0 | 8 hours | 1st and 2nd electrode structures | None |

Table 5 shows the results on drug absorbability obtained in these Examples and Comparative Examples. Comparing Examples 8 and 9 and Comparative Example 4 of one-way energization, absorption was significantly higher in Example 9 with energization than Comparative Example 4 without energization. Furthermore, absorption was increased as an energization period increased (for drug absorption, 4-hour energization<8-hour energization). In Examples 10, 11 and 12 and Comparative Example 5 of two-way polarity-inverting energization, as was in the one-way energization group, absorption was significantly higher in Examples 10, 11 and 12 with energization than Comparative Example 5 without energization. Furthermore, absorption was increased as an energization period increased (for drug absorption, 4-hour energization=8-hour energization). On the other hand, in Example 9 where the first electrode structure contained a drug, there was observed tendency to voltage increase presumably due to exhaustion of the electrode during iontophoresis energization, while in polarity inverting energization there was no variations in a voltage during energization. In these Examples, skin irritation was not observed after iontophoresis, suggesting that this energization method is effective as a local therapy.

Table 6 shows the results of therapeutic effect on a rabbit artery obstruction model in Examples 8 and 10 and Comparative Examples 4 and 5. In Examples 8 and 10, progress of a lesion was considerably inhibited in comparison with a non-energization group, Comparative Examples 4 and 5 to obtain a high therapeutic effect. Comparing Examples 8 and 10, slightly higher therapeutic effect was observed in polarity inverting energization. It was confirmed that a device according to the present invention is effective in iontophoresis of prostaglandin E1 in a local site.

TABLE 5

| Experimental Example 3 | Total absorption (μg)/dose (μg) | Energization status |
|---|---|---|
| Example 8 | 59.2/250.0 | No variation |
| Example 9 | 128.8/250.0 | Tendency to voltage increase |
| Example 10 | 192.3/500.0 | No variation |
| Example 11 | 262.1/500.0 | No variation |
| Example 12 | 240.8/500.0 | No variation |
| Comparative Example 4 | 20.7/250.0 | No energization |
| Comparative Example 5 | 103.7/500.0 | No energization |

TABLE 6

| Experimental Example 3 | Therapeutic effect | Energization status | Skin irritation |
|---|---|---|---|
| Example 8 | + to ++ | No variation | None |
| Example 10 | ++ | No variation | None |
| Comparative Example 4 | − | No energization | None |
| Comparative Example 5 | − | No energization | None |

Experimental Example 4

In Experimental Example 4, effect of a polarity inverting period on polarity-inverting iontophoresis of prostaglandin E1 was evaluated on the basis of a drug absorption in single dosing. In evaluation of a drug absorption in single dosing, Japanese white male rabbits (body weight: 2.5 to 3.0 kg) were used and the hair of the animals was removed on their ear skin with an animal clipper. After attaching the electrode structures of Examples and Comparative Examples, the system was electrified according to each Example. At the end of energization, an amount of the remaining drug in the device was determined by high performance liquid chromatography. The drug absorption was calculated by subtracting the remaining amount from the initial content.

In Examples 13 to 15, the first and the second electrode structures contained a prostaglandin E1·α-cyclodextrin clathrate compound (each electrode used was a silver/silver chloride electrode). In the Examples, pulse depolarized direct current was applied by a short-cut switch (frequency: 50 kHz; duty: 50%) for 4 hours, with a polarity inversion period of 1 min to 2 hour while in Comparative Example 6 the system was electrified polarity inversion for 4 hours. In the first and the second electrode structures, a stacked device filled with a 3.0 w/w% agar gel containing 0.2 w/w% sodium chloride (an electrode used was a printed electrode comprising silver/silver chloride electrode). A membrane containing cellulose acetate (manufactured by Advantech Inc., CMF film) was used as separation-retaining means. Then, 250 μg of a prostaglandin E1·α-cyclodextrin clathrate compound was dried and fixed. Before use, the gel was in contact with the membrane and used. Table 7 shows details of these Examples and Comparative Examples.

TABLE 7

| Experimental Example 4 | Energization | Constant Current value (mA/cm²) | Total energization or adhesion time | Drug-containing device | Polarity inversion period |
|---|---|---|---|---|---|
| Example 13 | Energized | 0.05 | 4 hours | 1st and 2nd electrode structures | 1 min |

TABLE 7-continued

| Experimental Example 4 | Energization | Constant Current value (mA/cm$^2$) | Total energization or adhesion time | Drug-containing device | Polarity inversion period |
|---|---|---|---|---|---|
| Example 14 | Energized | 0.05 | 4 hours | 1st and 2nd electrode structures | 1 hour |
| Example 15 | Energized | 0.05 | 4 hours | 1st and 2nd electrode structures | 2 hours |
| Comparative Example 6 | Energized | 0.05 | 4 hours | 1st and 2nd electrode structures | None |

Table 8 shows the results obtained in these Examples and Comparative Examples. In this Experimental Example, a printed electrode was used as an electrode in the light of practicability. As a result, iontophoresis with a polarity inverting period of 1 min to 2 hours in Examples 13 to 15 exhibited considerably higher absorbability than non-electrified Comparative Example 6. On the other hand, voltage increase was not observed in Examples 13 and 14 during energization, while in Example 15 where an inverting period was relatively longer, tendency to increase in a voltage was observed. For 4-hour polarity inverting period in Comparative Example 6, the system became insulated state after voltage increase caused by electrode exhaustion during application of iontophoresis. It is presumably because the use of the printed electrode might lead to a reduced time of voltage increase which is different from a silver/silver chloride wafer electrode.

TABLE 8

| Experimental Example 4 | Total absorption (μg)/dose (μg) | Energization status |
|---|---|---|
| Example 13 | 65.5/500.0 | No variation |
| Example 14 | 97.0/500.0 | No variation |
| Example 15 | 41.7/500.0 | Tendency to voltage increase |
| Comparative Example 6 | 4.6/500.0 | Insulating state after voltage increase |

Experimental Example 5

In Experimental Example 5, an optimal administration method in iontophoresis of prostaglandin E1 was evaluated on the basis of therapeutic effect using an artery obstruction model. The experimental procedure was as described in Experimental Example 3. Drug administration (for example, administration frequency and administration site) was conducted according to Examples and Comparative Examples as illustrated in Table 9. In Examples 16 and 17 and Comparative Examples 7 and 9, the first electrode structure contained a prostaglandin E1·α-cyclodextrin clathrate compound (the electrode used was a silver/silver chloride electrode). In Examples 16 and 17, pulse depolarized direct current was applied by a short-cut switch (frequency: 50 kHz; duty: 50%) for 4 hours while in Comparative Examples the system was left without energization for 4 hours. In Examples 18 and 19 and Comparative Example 8, the first and the second electrode structures contained a prostaglandin E1·α-cyclodextrin clathrate compound (each electrode used was a silver/silver chloride electrode). In the Examples, pulse depolarized direct current was applied by a short-cut switch (frequency: 50 kHz; duty: 50%) for 4 hours, with a polarity inversion period of one hour while in Comparative Example the system was left without energization for 4 hours. In the first and the second electrode structures, a stacked device filled with a 3.0 w/w% agar gel containing 0.2 w/w% sodium chloride (an electrode used was a silver/silver chloride electrode). A membrane containing cellulose acetate (manufactured by Advantech Inc., CMF film) was used as separation-retaining means. Then, 250 μg of a prostaglandin E1·α-cyclodextrin clathrate compound was dried and fixed. Before use, the gel was in contact with the membrane and used.

Japanese white male rabbits (body weight: 2.5 to 3.0 kg) were used and the hair of the animals was removed on their right ear with an animal clipper. Sodium laurate (5 mg, a 5% ethanol-containing isotonic phosphate buffer) was injected from its posterior auricular artery to induce peripheral artery obstruction. Each prostaglandin E1-containing formulation was applied around an obstruction site three times a week for Examples 16 and 18, seven times a week for Examples 17 and 19, and once a week for Comparative Examples 7 and 8. For Comparative Example 9, the drug was administered seven times a week on the opposite ear to that on which sodium laurate was applied. Healing of a lesion was visually observed after 7 days on the basis of the criteria in Table 3.

TABLE 9

| Experimental Example 5 | Constant Current (mA/cm$^2$) | Total energization time | Drug-containing device | Administration frequency | Administration site |
|---|---|---|---|---|---|
| Example 16 | 0.10 | 4 hours | 1st electrode structure | 3 Days/week | Around a lesion |
| Example 17 | 0.10 | 4 hours | 1st electrode structure | 7 Days/week | Around a lesion |
| Example 18 | 0.10 | 4 hours | 1st and 2nd electrode structures | 3 Days/week | Around a lesion |
| Example 19 | 0.10 | 4 hours | 1st and 2nd electrode structures | 7 Days/week | Around a lesion |
| Comparative Example 7 | 0.10 | 4 hours | 1st electrode structure | 1 Day/week | Around a lesion |
| Comparative Example 8 | 0.10 | 4 hours | 1st and 2nd electrode structures | 1 Day/week | Around a lesion |
| Comparative Example 9 | 0.10 | 4 hours | 1st electrode structure | 7 Days/week | Opposite side |

The results obtained in the above Examples and Comparative Examples are shown in Table 10. As seen from the table, Examples 16 and 17, Comparative Example 7, Examples 18 and 19 and Comparative Example 8 showed therapeutic effect depending on an administration frequency (a day a week<three days a week ≦ seven days a week. By comparison between iontophoresis groups of Examples 16 and 17 (one-way energization) and Examples 18 and 19 (two-way polarity inverting energization), there was observed tendency to higher therapeutic effect in polarity inverting energization. In particular, once-a-week administration as in Comparative Examples 7 and 8 did not exhibit adequate therapeutic effect while application to a site other than a lesion as in Comparative Example 9, there was not substantially observed systemic therapeutic effect.

TABLE 10

| Experimental Example 5 | Therapeutic effect | Skin irritation |
| --- | --- | --- |
| Example 16 | ± | None |
| Example 17 | + to ++ | None |
| Example 18 | ± to + | None |
| Example 19 | ++ | None |
| Comparative Example 7 | − | None |
| Comparative Example 8 | − | None |
| Comparative Example 9 | − | None |

INDUSTRIAL APPLICABILITY

According to an iontophoresis device of the present invention, a prostaglandin exhibiting therapeutic effect in a local site may be used and stabilizing means may be chemically or mechanically (into a device) incorporated to give a system exhibiting good drug stability during storage and giving effective and continuous absorption even in a small amount of a drug added. By combining constant current means and polarity inverting means, conductivity can be maintained for a long period and a drug may be transdermally delivered with higher bioavailability and good reproducibility. Constant current means and polarity inverting means may also increase a treatment area even in local therapy to give higher therapeutic effect in a local site. Furthermore, a device according to the present invention may deliver a drug with a higher efficiency from a local site to a patient with chronic artery obstruction such as Berger's disease and obstructive arteriosclerosis, vibration disease, progressive systemic sclerosis or systemic lupus erythematodes, which is difficult to be treated with an injection or oral drug, and is therapeutically thus quite useful.

What is claimed is:

1. An iontophoresis device which transdermally or transmucosally administers a prostaglandin, comprising:
    (a) a first electrode structure containing a prostaglandin;
    (b) a second electrode structure containing a prostaglandin; and
    (c) a power supply electrically connected between the first and second electrode structures and equipped with constant-current supplying means and polarity inverting means,
    wherein the first and the second electrode structures include stabilizing means for inhibiting hydrolysis of the prostaglandin during storage, the stabilizing means being a drug retainer which retains a prostaglandin in a dry condition, and wherein a stabilizing agent for chemically stabilizing a prostaglandin or a dissolution promoter is added to the stabilizing means, and
    wherein the power supply conducts energization with a polarity inverting period of 1 minute to 2 hours.

2. The iontophoresis device according to claim 1, wherein the power supply conducts a continuous energization with direct current, pulse direct current, or pulse depolarized direct current for 1 hour to 48 hours in total.

3. The iontophoresis device according to claim 1, wherein at least one of a surfactant for promoting drug delivery and a water-soluble cyclodextrin is added to the prostaglandin.

4. The iontophoresis device according to claim 1, wherein the power supply applies pulse dc voltage of 0.1 to 200 kHz between the first and the second electrode structures.

5. The iontophoresis device according to claim 2, wherein the power supply conducts the continuous energization for a period of 3 to 7 days/week.

6. A method of transdermally or transmucosally administering a prostaglandin via an iontophoresis device having a first electrode structure containing a prostaglandin, a second electrode structure containing a prostaglandin, and a power supply electrically connected between the first and second electrode structures and equipped with constant-current supplying means and polarity inverting means, the first and the second electrode structures including stabilizing means for inhibiting hydrolysis of the prostaglandin during storage, the stabilizing means being a drug retainer which retains a prostaglandin in a dry condition, and wherein a stabilizing agent for chemically stabilizing a prostaglandin or a dissolution promoter is added to the stabilizing means, the method comprising:
    applying the first and second electrode structures to an administration area of a patient,
    applying a direct current, pulse direct current, or pulse depolarized direct current from the power supply to the patient via the first and second electrodes for a direct current energization period of 1 to 12 hours; and
    inverting the polarity thereof for a polarity inverting period of 1 minute to 4 hours.

7. The method of claim 6, wherein the direct current, pulse direct current, or pulse depolarized direct current energization period is 4 to 12 hours, and the concurrent polarity inverting period is 1 minute to 2 hours.

8. The method of claim 6, wherein the direct current, pulse direct current, or pulse depolarized direct current energization period is about 4 hours, and the polarity inverting period is about 1 hour.

* * * * *